United States Patent

Roberts et al.

[11] Patent Number: 5,871,696
[45] Date of Patent: Feb. 16, 1999

[54] CASSETTE FOR BLOOD SMEAR SLIDES AND COOPERATIVE SLIDE EJECTION ASSEMBLY

[75] Inventors: Daniel B. Roberts, Miami; Raymond G. Krause, deceased, late of Pembroke Pines, by Patricia M. Krause, legal representative; Armando J. Valledor, Miami; Manuel Calvo, Miami, all of Fla.; Brian Scrivens, Colora, Md.

[73] Assignee: Coulter International Corp., Miami, Fla.

[21] Appl. No.: 896,038

[22] Filed: Jul. 17, 1997

Related U.S. Application Data

[63] Continuation of Ser. No. 557,230, Nov. 14, 1995, abandoned.

[51] Int. Cl.[6] .................................................. G01N 21/00
[52] U.S. Cl. ................................ 422/65; 422/64; 422/67; 118/100
[58] Field of Search .................................. 42/63, 65, 67, 42/64, 68.1; 436/47, 49; 118/100, 120, 238, 506

[56] References Cited

U.S. PATENT DOCUMENTS

| | | | |
|---|---|---|---|
| 3,683,850 | 8/1972 | Grabhorn | 118/100 |
| 4,096,824 | 6/1978 | Levine et al. | 118/100 |
| 4,319,542 | 3/1982 | Ojima et al. | 118/100 |
| 5,075,079 | 12/1991 | Kerr et al. | 422/64 |
| 5,081,038 | 1/1992 | Sugaya et al. | 436/46 |
| 5,209,903 | 5/1993 | Kanamori et al. | 422/65 |
| 5,356,595 | 10/1994 | Kanamori et al. | 422/65 |

*Primary Examiner*—Harold Y. Pyon
*Attorney, Agent, or Firm*—Warren W. Kurz

[57] ABSTRACT

A cassette for blood smear slides has a holder portion for supporting slides in a stack and an alignment surface for orienting a bottom slide with respect to a slide egress window. A force plate member is urged against the top slide in the stack with a constant force spring to align the bottom slide and to retain the slide stack. A slide extraction device is constructed to enter the cassette and has follower pins which ride on cam surfaces of the cassette to precisely position detent edges vis a vis an edge of a bottom slide of the stack. The cassette also has structure for signaling an empty condition.

11 Claims, 9 Drawing Sheets

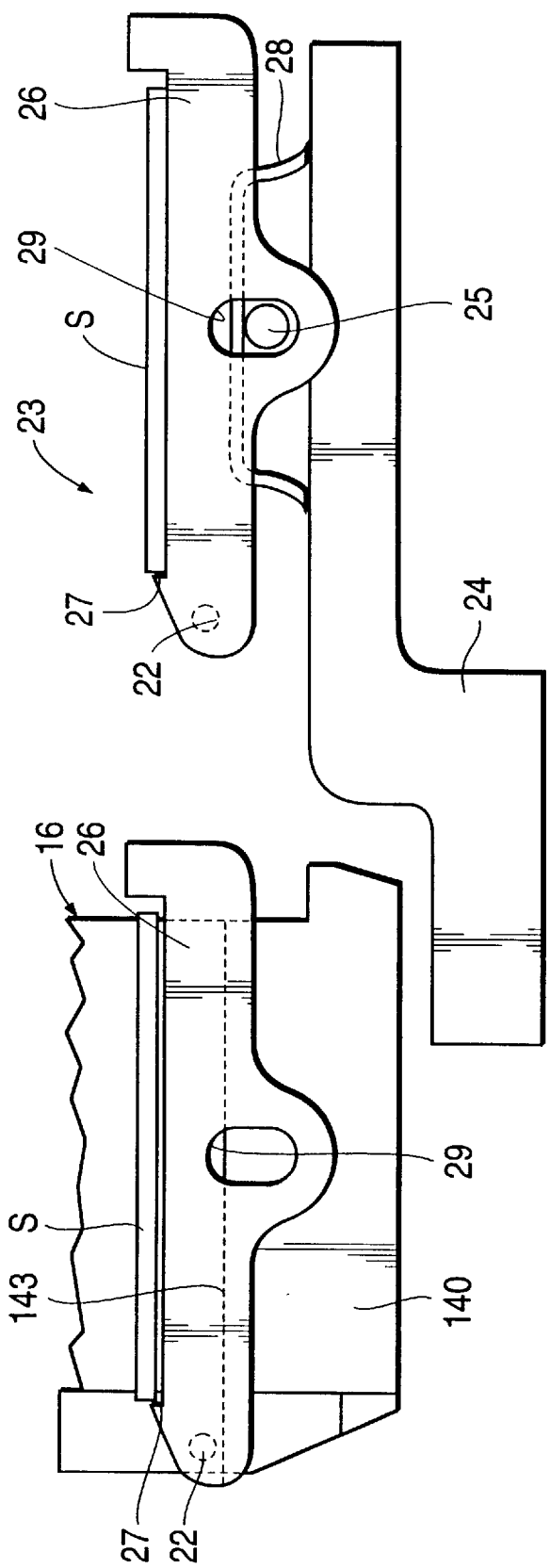

5,871,696

CASSETTE FOR BLOOD SMEAR SLIDES AND COOPERATIVE SLIDE EJECTION ASSEMBLY

This is a Continuation of U.S. application Ser. No. 08/557,230 filed Nov. 14, 1995, now abandoned.

CROSS REFERENCE TO RELATED APPLICATIONS

Reference is made to commonly assigned U.S. application Ser. No. 08/557,226, filed Nov. 14, 1995 entitled "Improved Apparatus and Method for Automated Production of Blood Smear Slides", now abandoned.

BACKGROUND OF INVENTION

1. Field of Invention

The present invention relates to cassettes for holding and dispensing a plurality of microscope slides, such as are used for blood smear specimens, and more particularly to improved constructional features of such cassettes and of a cooperative slide ejection assembly of apparatus for automatically producing blood smear slides.

2. Background Art

The above-noted U.S. application Ser. No. 08/557,226, describes apparatus for automatically producing a plurality of blood smear specimens respectively upon a succession of glass microscope slide elements supplied to the apparatus. In order to operate in a reliable fashion, this apparatus requires a system for reliably providing a plurality of slides seriatim into a predetermined ingress orientation for precise pick up and handling by the operative stations of the automated slidemaker. Such slides are marketed in a plurality of different packages. To assure proper slide supply, it is desirable to have a cassette that is conveniently loadable with a large number, e.g. 100, of slides from those packages, and that will safely store those slides during handling and insertion into the slidemaker apparatus. The cassette also should interfit and cooperate with the automated slidemaker in: (i) assuring reliable, single-slide ejections to provide an unbroken succession of slides and (ii) signaling the apparatus promptly upon the cassette becoming empty.

U.S. Pat. No. 5,209,903 describes one cassette construction that is intended to achieve safe slide storage, reliable feed and empty detection capabilities. This cassette has a bottom outlet passage for slide feed; and, in order to prevent slides from falling out of this passage, provides a cassette shutter member that must be opened by the slidemaker apparatus. However, the slide stack remains loose within the cassette, necessitating careful handling of the cassette. The '903 patent system utilizes special slides, having a frosted area for data printing, and a photodetector on the slide ejection mechanism senses such frosted area to determine a cassette-empty condition. While the cassette and slide ejection system of the '903 patent appears quite functional, it would be desirable to have a system which retains and controls a slide stack more effectively and which does not require special slide characteristics to signal a cassette-empty condition.

SUMMARY OF INVENTION

One important object of the present invention is to provide a slide cassette and slide ejection assembly that cooperate to achieve improved slide storage and reliable slide supply. Another object of the present invention is to provide such a cassette that is easily loaded by machine operators or their assistants. Another object of the present invention is to provide a slide cassette that provides a reliable signal when the last slide is ejected therefrom. The system of present invention provides significant advantage from the viewpoints of retaining a slide stack within the cassette with a consistent force toward the cassette's slide egress and consistently feeding single slides into a precise orientation for pickup by a slide manipulation assembly of an automated blood smear slide making apparatus.

In one aspect the present invention constitutes an improved cassette for use in an automated blood smear slide apparatus having a cassette mount and means for ejecting slides from a mounted cassette into an operative orientation in said apparatus. The cassette comprises: (i) a slide holder portion configured to position slides in an ordered stack, (ii) a cover portion mounted on said holder portion for movement between an open position for stack loading and a position enclosing a loaded stack, (iii) alignment means coupled to a bottom region of said holder portion for aligning slides for ejection from said cassette and (iv) means mounted in said cover portion for exerting a substantially constant force urging a slide stack toward said alignment means, when said slide holder portion is in said enclosing position.

In another aspect the present invention constitutes a slide ejection system for an apparatus that automatically produces blood smear slides and that comprises a slide cassette mount, means for ejecting slides from a mounted cassette and means for precisely grasping and manipulating an ejected slide to effect blood smear slide production. Such a system includes (a) a slide cassette having: (i) walls forming a slide stack cavity, (ii) alignment means for orienting the bottom slide of a stack within said cavity, (iii) means for urging a stack toward said alignment means and (iv) cam means for directing movement of a slide ejection carriage within said cassette; and (b) a slide ejection carriage, mounted for movement between an ejection position within a received cassette and a pick-off position wherein said manipulation means grasps an ejected slide therefrom and including: (i) a slide support surface, (ii) means for detenting a slide on said support surface and (iii) follower means for following said cam means to control the positions of said support surface and detenting means during ejection movements of said carriage.

BRIEF DESCRIPTION OF DRAWINGS

The subsequent description of preferred embodiments of the invention is made with reference to the accompanying drawings wherein:

FIGS. 8, 9A and 9B are enlarged views of the slide ejection system showing a slide ejection operation.

DETAILED DESCRIPTION OF THE INVENTION

Figure 1:
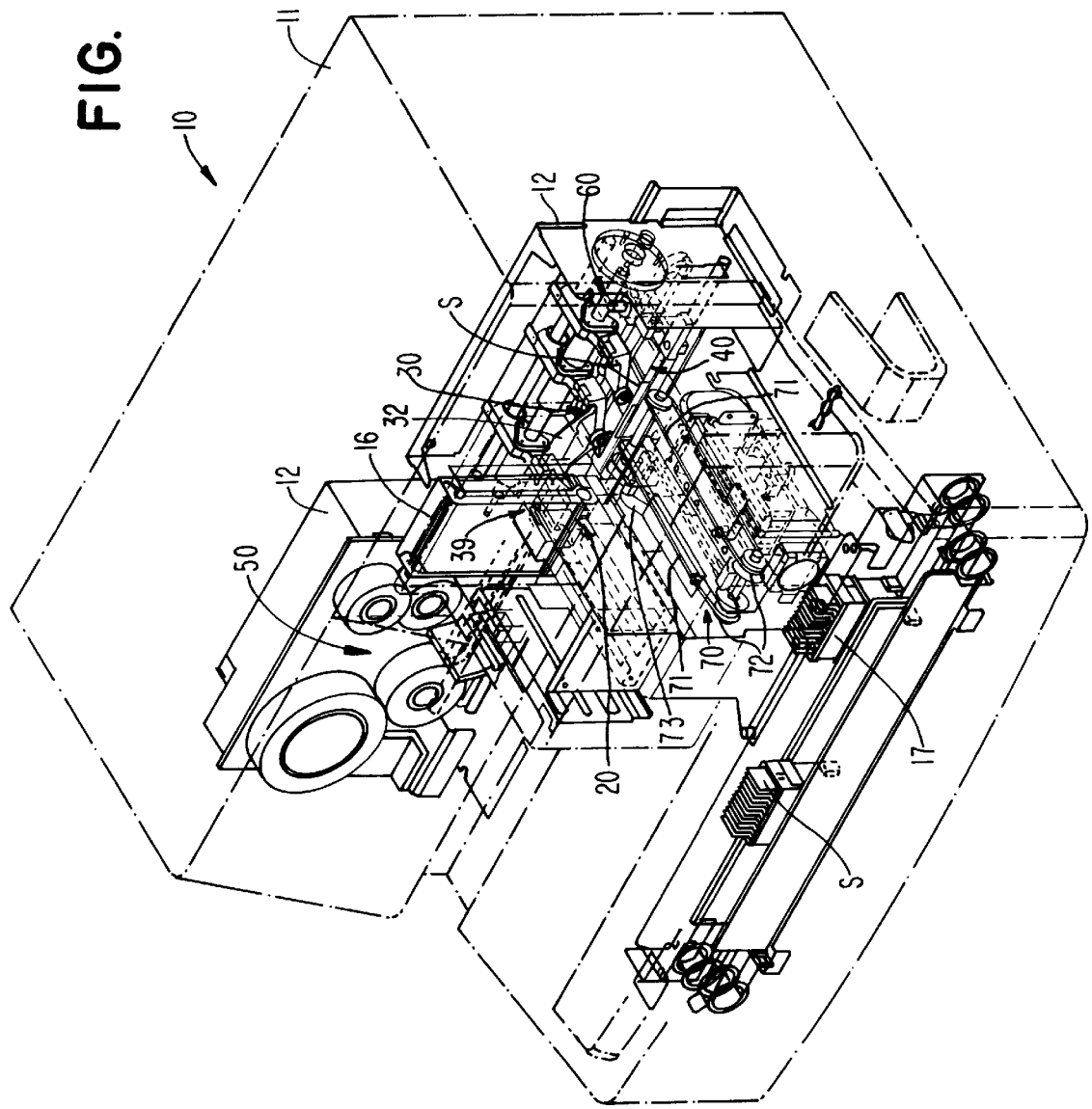
FIG. 1 is a perspective view of an apparatus for automatically producing blood smear slides, incorporating a slide cassette and ejection system according to the present invention.

Referring to FIG. 1 it can be seen that the automated slide maker apparatus 10 comprises a number of cooperative assemblies, located within a housing 11 and supported on a mainframe 12, that perform different functions on specimen substrates S (e.g. 1"×3"×0.04" microscope slides), which are received from cassettes 16 and outloaded into baskets 17. In general the apparatus 10 comprises a slide ejection assembly 20, a slide manipulation assembly 30, a slide transport assembly 40, a slide marking assembly 50, a drop dispensing assembly 60 and dryer assembly 70, all operating under the contact of a machine control systems (e.g. a microprocessor with cooperative RAM and ROM memories and related timing control and interrupt, input and output interface sections).

As described in the above-noted U.S. application Ser. No. 08/557,226, an initial slide is ejected from cassette 16 by assembly 20 and moved onto platform 39, where it is picked-up and moved onto transport assembly 40 by assembly 30, which moves up ramp 32. The transport assembly 40 moves the slide S to the marking station 70 where a specimen identification label L is attached to one end region. The slide is then moved (rightward as viewed in FIG. 1) to receive a blood specimen drop from assembly 60, and thence to the smear position shown in FIG. 1. During identifying and dispensing operations on the first slide, a second slide is extracted by assembly 20 and manipulated to an angular orientation (vis a vis the first slide) by assembly 30. The assembly 30 then moves to the angular slide's lower, end edge to contact the blood drop on the first slide and, after a pause to allow blood to flow to the edges of the interface region, moves it leftward to produce a blood smear on a first major surface of the specimen slide.

The specimen slide is then moved transversely off the transport assembly 40 onto the dryer apparatus 70. Because the manipulation assembly 30 of apparatus 10 uses the edges of successively ejected, grasped and manipulated slides S as the means for effecting blood drop spreading across preceding slides, the interfacing between the slide cassette 16, the slide ejection assembly and the slide manipulation assembly 30 becomes critical. Specifically, it is important that each slide be picked-up by assembly 30 in a correct location and orientation. Errors in the position of a grasped slide can cause the blood-drop spreading edge of that slide to be misoriented vis a vis the specimen-bearing-slide, resulting in an improper blood smear. Slide jamming, double feeding of slides and failure to stop operations when a slide cassette is empty, each also can cause significant problems.

Figure 2:
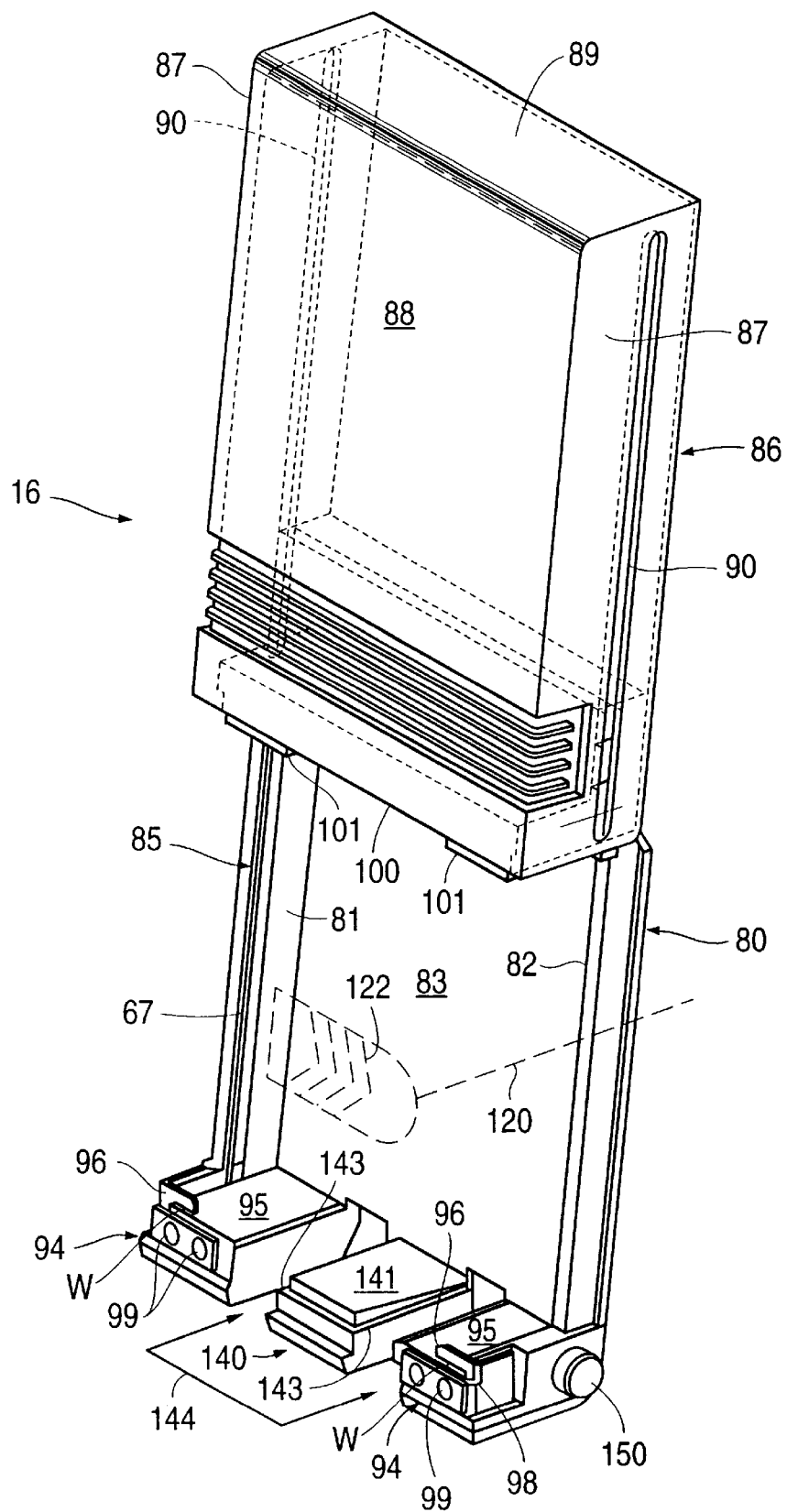
FIG. 2 is a perspective view of one preferred slide cassette according to the present invention, in an opened, slide-load position.
Figure 3A:
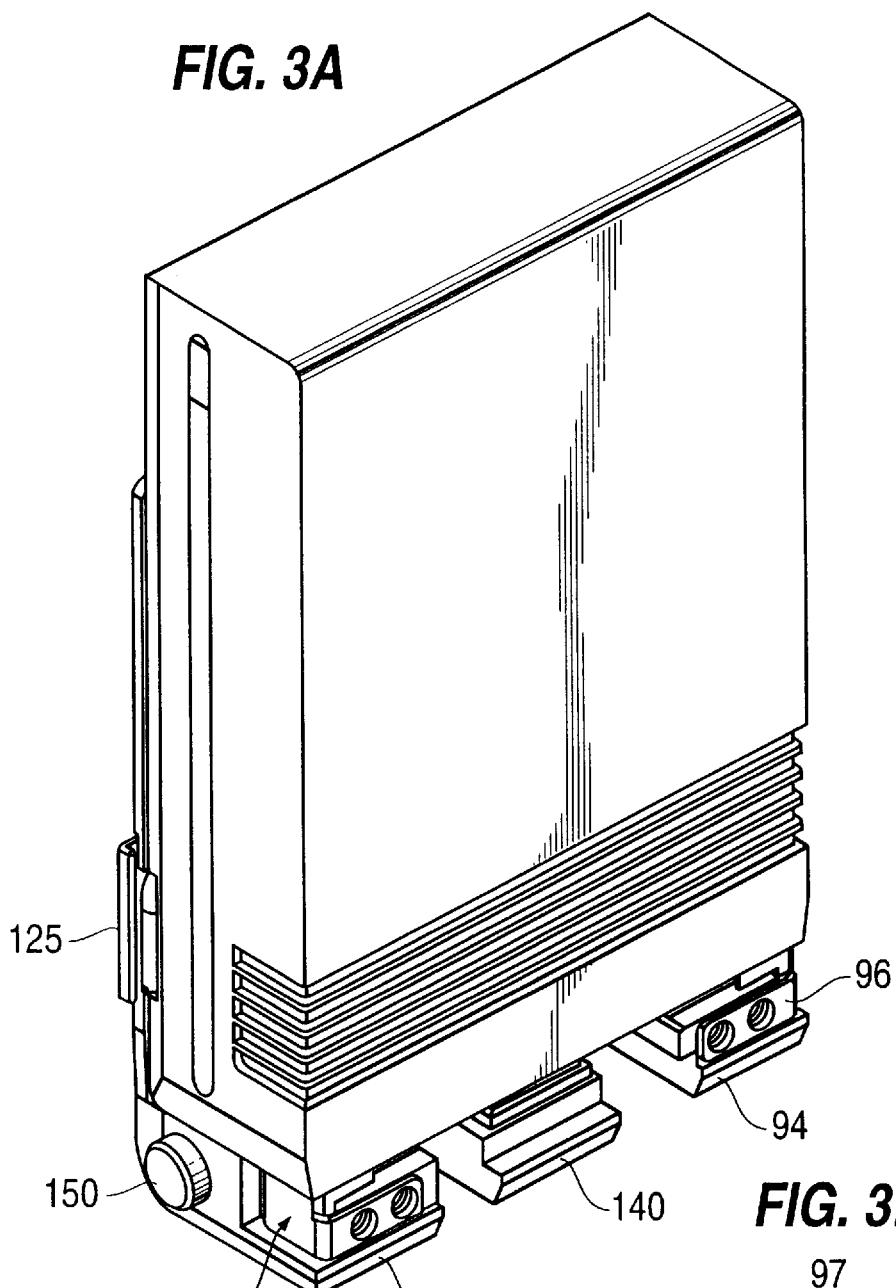
FIG. 3A is a perspective view of the FIG. 2 cassette in a closed position.
Figure 3B:
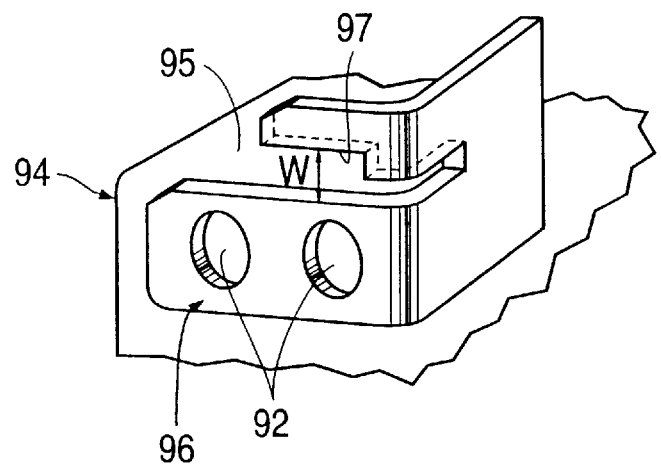
FIG. 3B is an enlarged perspective view of a portion of the FIG. 3A cassette.
Figure 4:
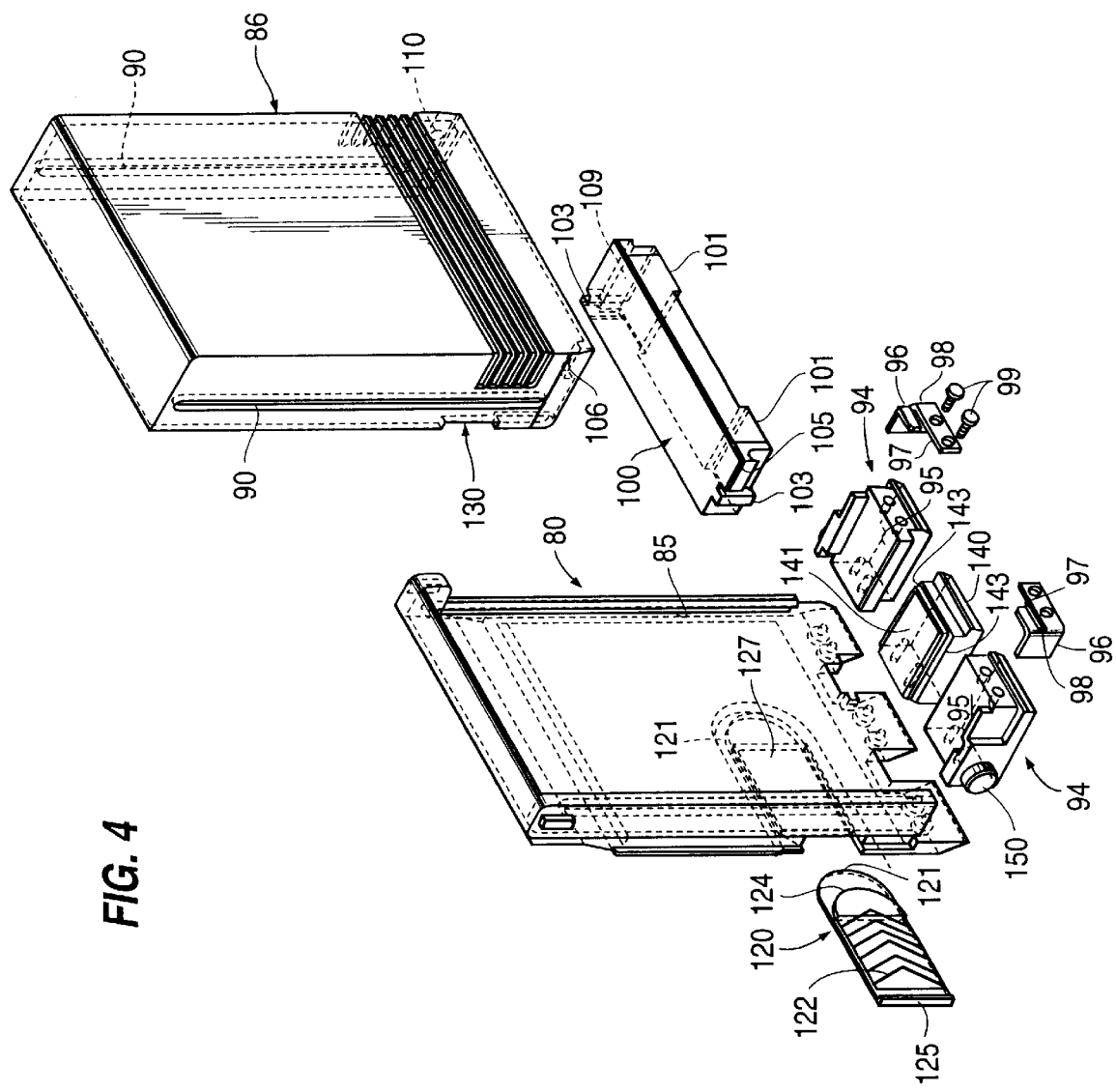
FIG. 4 is an exploded perspective view of the FIG. 2 slide cassette.
Figure 5:
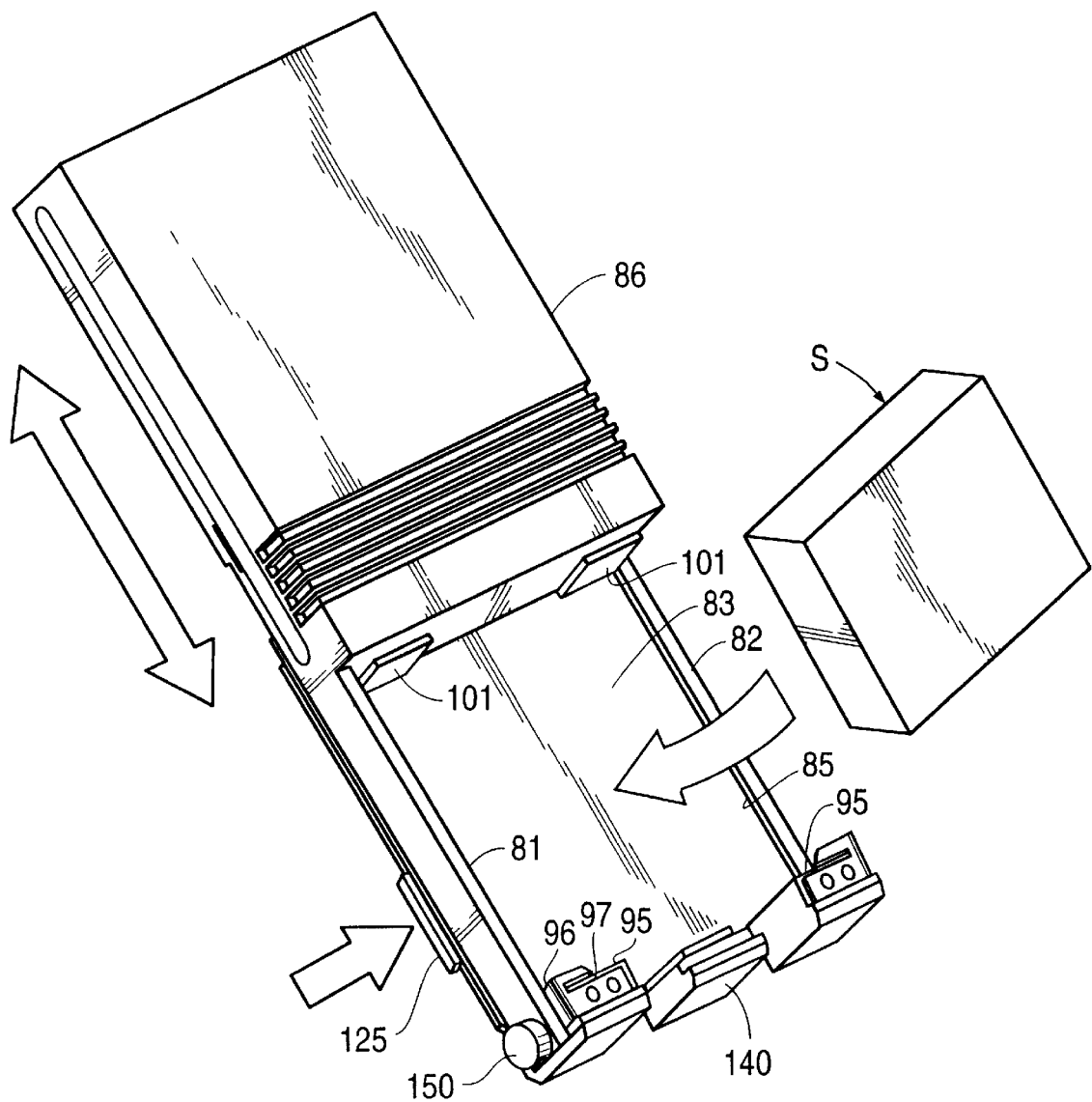
FIG. 5 is a schematic perspective illustrating a slide stack insertion operation.

The cassette 16 and slide ejection assembly 20 of the present invention function and cooperate in ways that obviate these problems. Referring to FIGS. 2–4, the slide cassette 16 comprises a main body portion 80 having side walls 81, 82 with side wall grooves 85 that define a slide alignment recess 83, which holds a stack of slides in an orderly manner, with their edges in alignment along normals to their face surfaces. A cassette cover portion 86 comprises side walls 87, front wall 88 and top wall 89. The interior of the side walls have longitudinal grooves 90 which ride along lugs 84 on the exterior of walls 81, 82, so that the cover position 86 can slide between a position that opens recess 83 for slide loading (shown in FIGS. 2 and 5) and a closed position enclosing and holding a stack of slides in the recess (shown in FIG. 3A).

Coupled to bottom regions of portion 80, in spaced relation, are slide stack support members 94, which each comprise a planar slide alignment surface 95 and have attached to the front thereof, e.g. with screws, metal gates 96 defining slide egress windows W, that are sized to permit the passage of single slides. As shown in detail in FIG. 3B, the gates 96 each have a flange surface 98 that is generally offset from, but precisely located with respect to, the window edge 97 and flange surfaces 98 are adapted to rest on alignment surfaces 95 to precisely locate the gates vis a vis the alignment surfaces. As shown in FIG. 3B, openings 92 in the gates are elongated so that the flange can seat on surface 95 before the tightening of the screws. Thus the precise notch defining the window W in the gate provides an easy to fabricate and assemble construction for reliable passing of single slides, without double feed.

Figure 6:
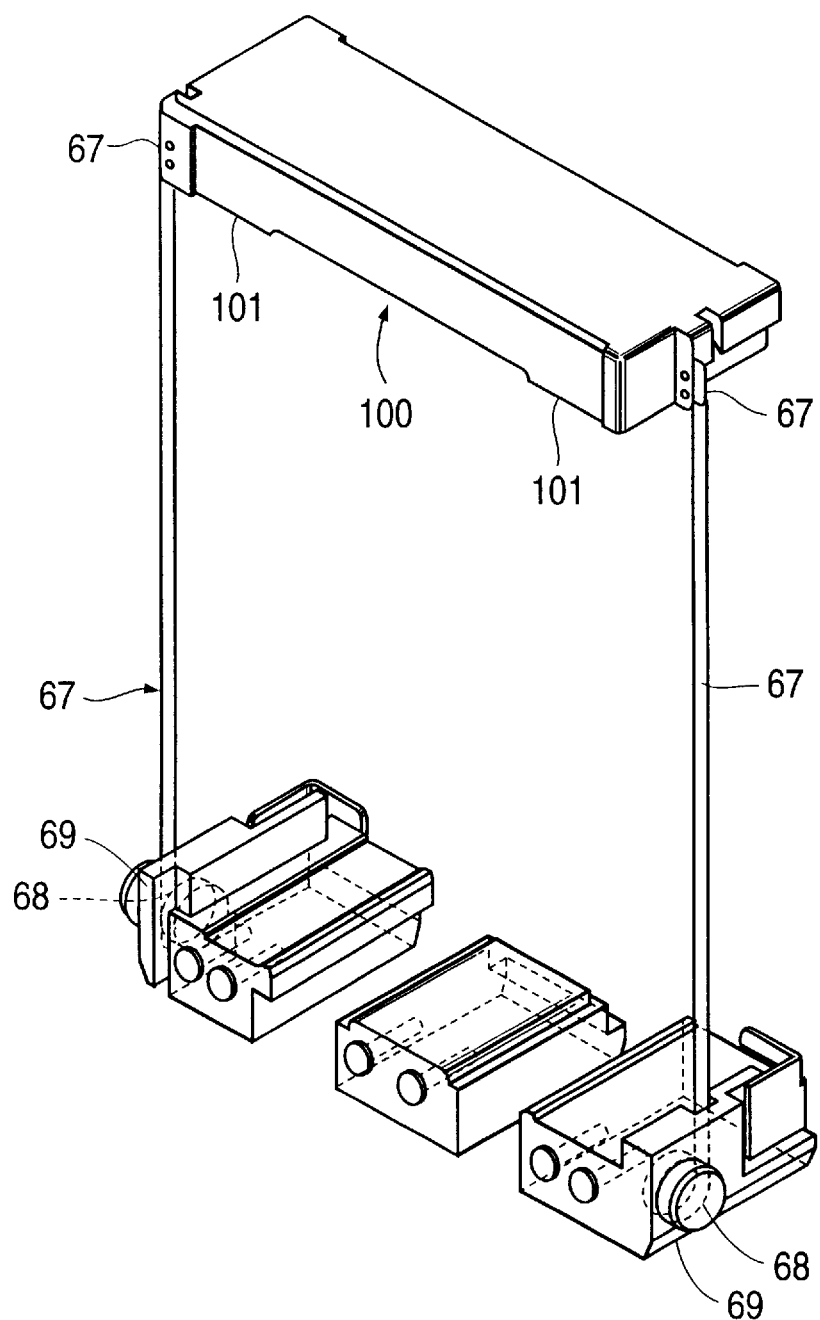
FIG. 6 is an exploded perspective view of portions of the slide cassette.

To provide pressure for urging the slide stack toward the alignment surfaces 95, a force plate 100 having spaced shoe portions 101 is slidably mounted to move within cover 86 with the side lugs 103 following the side wall grooves 85 of main body portion 80, and means are provided to urge the force plate shoes 101 into engagement with the top of a slide stack supported in recess 83, with a constant spring force. Specifically a pair of Negator spring elements 67 are nested in the bottom sides 68 of the main body portion 80 beneath alignment surfaces 95, with their lower interior coil ends 69 loose and their outer coil ends 67 coupled to the sides of the force plate 100 inside lugs 103 (see FIG. 6). It will be appreciated that the springs alternatively can be mounted with the outer ends affixed to main body 80 and the spring coils nested in the ends of the force plate 100. When a stack of slides is within the recess, the coil extends to allow the force plate to move to the top of the cover (with the cover closed); and as slides are expended by subsequent ejections, the plate moves downward, maintaining a constant downward force on the stack. This unique construction enables adequate force with a small stack, yet non-excessive force with a full stack, as would be provided by compressive spring systems. In addition, this force maintains the stack in a retained condition (pinched between the force plate and surfaces 95) regardless of the amount of slides in the cassette. The lip 105 rests on lug 106 of the cover in a loading condition (see FIG. 4), to retain the force plate within the cover. When the cover section 86 is raised to open the cassette, lug 106 engages lip 105 to move the force plate upward to allow loading of slides. When the cover is closed the force plates remains at the top of the stack, exerting the constant force from springs 67.

In order to signal the control system of apparatus 10 that a slide cassette 16 is empty, a reflective region 109 is provided on one side of the exterior of the force plate 100. A cooperative opening 110 is located at the bottom of a side 87 of the cover portion 86 so that a photo detection system of apparatus 10 can illuminate through opening 110. When the last slide has been used, mark 109 will align with opening 110, as the force plate bottoms out, and a reflective signal to a photo detector then indicates the cassette is empty and should be replaced before commencing any further blood smear operations.

The cassette 16 also comprises a latch member 120 mounted to slide within a recess 121 on the back of the main body portion. The exterior surface of latch member 120 has molded surface regions 122 to facilitate an inward push (right as viewed in FIGS. 2 and 4) and has an integrally molded spring member 124, flexing against an abutment surface 127 formed in recess 121 so as to urge the member 120 toward a latch position (leftward as viewed in FIGS. 2 and 4). A latch end surface 125 is thereby urged to block the slide of cover 86, intercepting edge region 130 to retain the cover closed until the member 120 is push rightward and the cover lifted.

In order to effect reliable ejection and precise positioning of slides from the cassette 16, the main body portion has a central guide member 140 located between alignment members 94 with a top surface 141 slightly below surfaces 95. The guide member 140 has two cam surfaces 143, which are constructed to guide the ejection assembly 20 during the slide ejection process, as will be described after a brief overall description of the loading and insertion of a cassette with reference to FIG. 5. Thus, the cover 86 is lifted to the position shown in FIG. 5 and a stack of slides S is loaded into the recess 83 with their edges aligned by sides 81, 82 and the bottom slide resting on surfaces 95. The cover 86 is then moved downward and latched by member 120, and force plate 100 is moved downward by springs 67 so that its shoes 101 urge the bottom stack slide onto alignment surfaces 95. The cassette 16 is now loaded into a mounting tray 21 of ejection assembly 20 and locking hooks (not shown) engage with lugs 150 on the cassette to accurately position and hold the cassette with respect to slide ejection assembly.

Figure 7B:
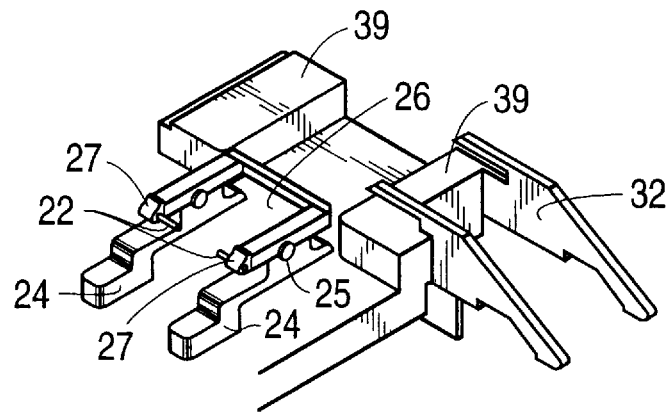
FIGS. 7A and 7B are perspective views of the slide ejection assembly of the FIG. 1 apparatus.
Figure 7A:
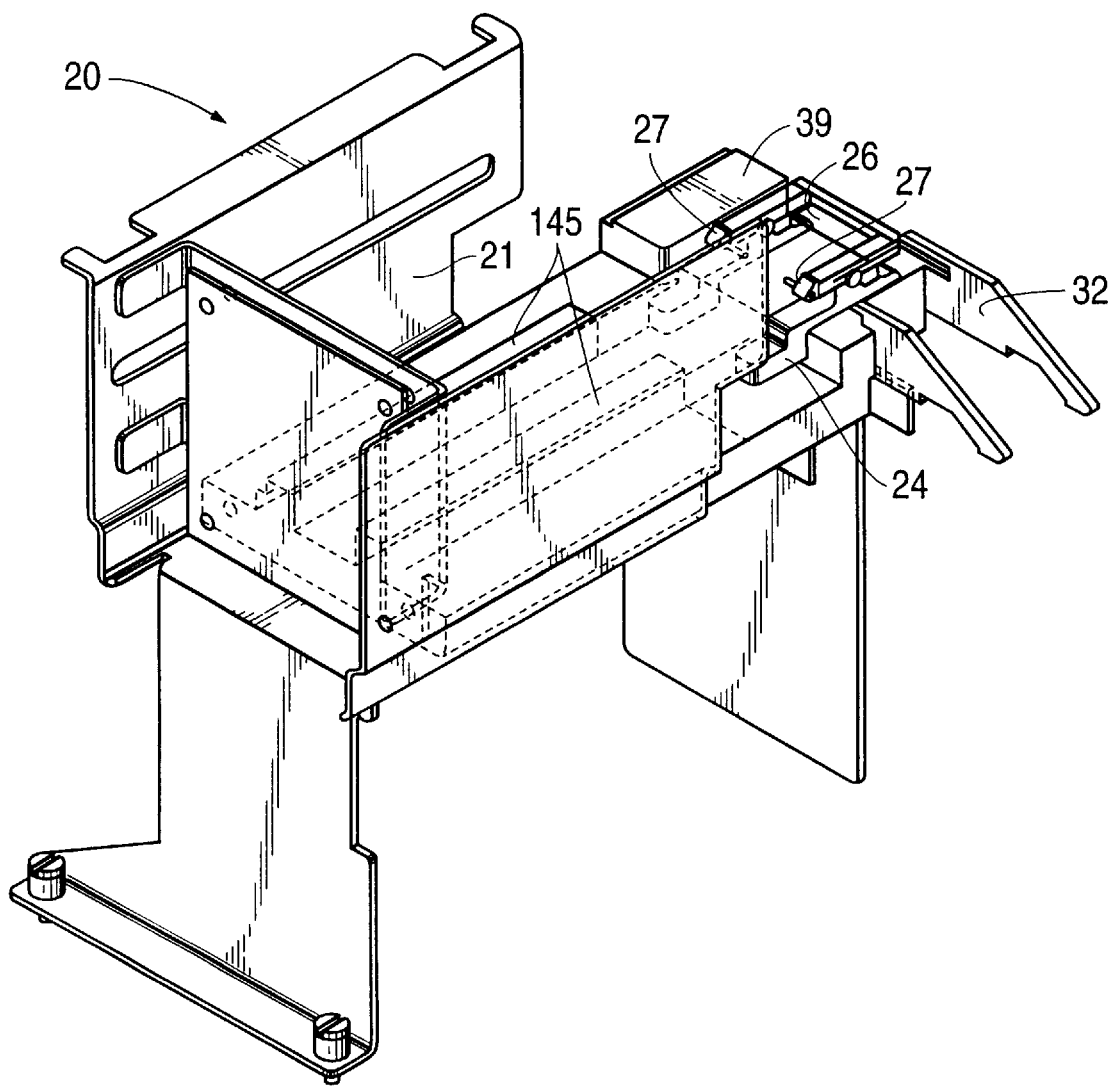
Figure 8:
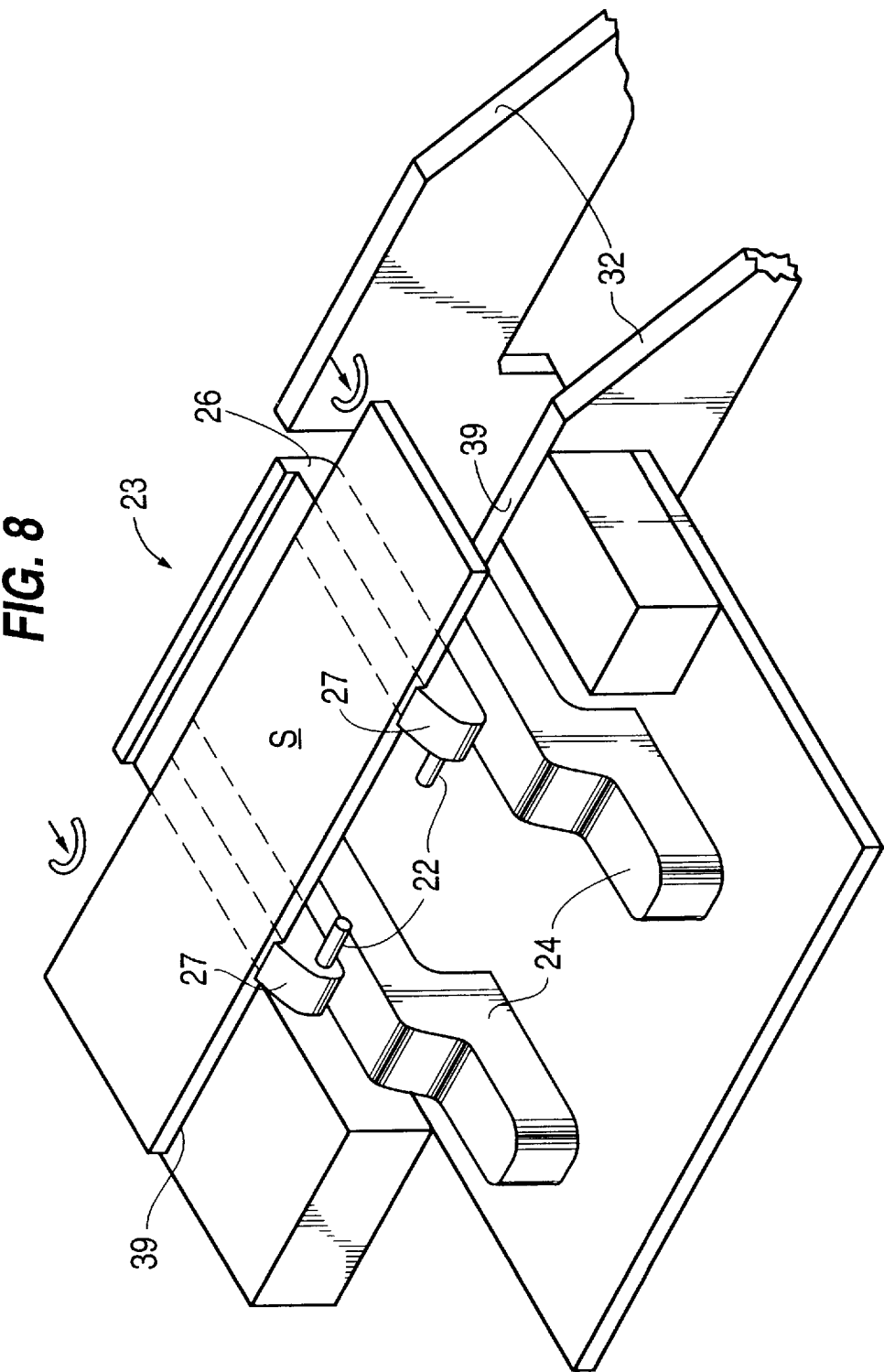

Referring to FIGS. 7A and 7B, the mounting tray 21 of assembly 20 is adapted to hold a plurality of cassettes 16 with the groove spaces 144, defined between cassette members 94 and 140, riding along rails 145 of the tray floor. Mounted for movement between the slide platform region 39 and the proximate tray region, is a slide extractor and cart assembly 23 (see FIGS. 8, 9A and 9B). Assembly 23 comprises two spaced slider members 24, constructed and located for reciprocatory movement into and out of the groove spaces 144 in the bottom of a positioned cassette, and coupled to drive means (e.g. an air cylinder coupled to the bottom of members 24) for selectively effecting such movements. A U-shaped extractor member 26 is centrally mounted on the sides of slider members 24, by pins 25, in a manner enabling its ends to rock up and down. The mount openings 29 in slider arms 24 are elongated, providing the extractor member the capability to tilt from side to side, also. Each of the top surfaces of the U ends has a detent edge 27, and the member 26 is urged to a flat orientation by leaf springs 28, but can move substantially universally, at the region of mount pins 25, to allow guide pins 22 (extending normally from the interior walls of the U ends) to follow the cam surfaces 143 of a positioned cassette.

During an extraction operation, the drive means for slider arms 24 is actuated to move the arms and the extractor member 26 coupled thereto, into a mounted slide cassette 16, to the positions shown in FIGS. 7B and 9B. As shown best in FIG. 9B, the guide pins 22 follow along cam surfaces 143 (see also FIG. 2) of the cassette 16 to accurately position the detent edges 27 vis a vis the cassette and thus with respect to a bottom slide therein. When the slider arm drive means is actuated to withdraw the assembly 23, the detent edges 27, strip the bottom slide from the stack and pull it through the windows W of the cassette. In one preferred embodiment, the cam surfaces 143 slant downwardly toward the exit side of the cassette so that the extractor member 26 will slant an exiting slide about 2o below the horizontal, to facilitate separation from the stack. When the slide has been moved to the FIG. 9A position, it can be picked up from platform 39 by the slide manipulation assembly 30. To accurately position the slide, spring members 55 are located to abut a slide edge and maintain the opposite edge in contact with d[0089]tentes 27.

The invention has been described with reference to particular preferred embodiments, but it will be understood that variations and modifications can be effected within the spirit and scope of the invention.

We claim:

1. A microscope slide cassette comprising:
   (a) a main body portion having a central recess configured to receive and position a stack of rectangular microscope slides with their respective edges aligned on normals to their face respective surfaces;
   (b) a cover portion having wall means for selectively enclosing a stack of slides received by said main body portion, said cover portion being slidably mounted on said main body portion for movement between a first position in which said cover portion is displaced from said central recess to enable slides to be received by said main body portion, and a second position in which said wall means covers said central recess;
   (c) alignment means coupled to a bottom end of said main body portion for precisely orienting a face surface of a microscope slide urged thereagainst;
   (d) a force plate slidably mounted on said main body portion for movement in the directions of said normals and into contact with a face surface of a top slide of a stack received by said recess; and
   (e) constant force spring means interconnecting said force plate and said main body portion for urging said force plate toward said alignment means; wherein said spring means comprises a pair of coil springs, each having one end attached to said force plate, and an opposite end attached to said main body portion.

2. The invention defined in claim 1 wherein said spring means comprise two thin strip spring coils seated, with loose inner ends, at opposite bottom-side regions of said main body portion, said coils having outer strip ends attached to opposite side regions of said force plate.

3. The invention defined in claim 1 further comprising gate means, coupled to said bottom end of said main body portion for forming a single-slide passage that prevents multi-slide ejections from said cassette.

4. The invention defined in claim 3 wherein said gate means includes an abutment surface for precisely aligning said passage vis a vis said alignment means.

5. The invention defined in claim 1 wherein said alignment means form a passage for a slide ejection carriage to pass beneath a slide positioned thereon.

6. The invention defined in claim 5 further comprising guide means, coupled to the bottom of said main body portion, for guiding the path of movement of a slide ejection carriage to eject the bottom slide from the stack with its major surface at a slight negative angle to the slide orienting surface defined by said alignment means.

7. The invention defined in claim 1 further comprising signal means on a side wall of said force plate for indicating a slide empty condition.

8. The invention defined in claim 7 further comprising a detector passage formed in the side of said cover portion for allowing photodetection of the position of signal means.

9. The invention defined in claim 1 further comprising latch means mounted on said main body portion and notch means formed on said cover in a position to interfit with said latch means and retain said cover in a closed condition.

10. The invention defined in claim 9 wherein said latch means comprises a slider recess molded in said main body portion and a latch slider mounted in said recess and having an integrally molded spring portion urging said slider to a latch position.

11. A microscope slide cassette construction comprising:
(a) a main body portion having a central recess configured to receive and position a plurality of rectangular slides with their edges aligned on normals to their face surfaces;
(b) alignment means coupled to a bottom end of said main body portion for precisely orienting a major surface of a slide urged thereagainst;
(c) a force plate slidably mounted on said main body portion for movement in the directions of said normals and into contact with the major surface of a top slide of a stack loaded in said recess; and
(d) constant force spring means for urging said force plate toward said alignment means; wherein said spring means comprises a pair of coil springs, each having one end attached to said force plate, and an opposite end attached to said main body portion.

* * * * *